United States Patent
Carpenter et al.

(10) Patent No.: US 8,999,239 B2
(45) Date of Patent: Apr. 7, 2015

(54) SYSTEM, DEVICE AND METHOD FOR REDUCING LUMINESCENCE OUTPUT SHIFTS

(75) Inventors: William Carpenter, Stony Point, NY (US); Martin Fletcher, Hopewell Junction, NY (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 1260 days.

(21) Appl. No.: 12/092,277

(22) PCT Filed: Nov. 16, 2006

(86) PCT No.: PCT/US2006/044630
§ 371 (c)(1),
(2), (4) Date: May 1, 2008

(87) PCT Pub. No.: WO2007/061825
PCT Pub. Date: May 31, 2007

(65) Prior Publication Data
US 2008/0261324 A1 Oct. 23, 2008

Related U.S. Application Data

(60) Provisional application No. 60/737,650, filed on Nov. 17, 2005.

(51) Int. Cl.
*G01N 21/76* (2006.01)
*G01N 35/10* (2006.01)
*B01L 3/02* (2006.01)
*G01N 35/00* (2006.01)

(52) U.S. Cl.
CPC .......... *G01N 35/1095* (2013.01); *B01L 3/0241* (2013.01); *G01N 21/76* (2013.01); *B01L 2200/14* (2013.01); *B01L 2400/0439* (2013.01);
(Continued)

(58) Field of Classification Search
CPC ........ A61B 5/14539; C12N 9/14; C12N 9/86; C12N 13/00; C12N 2533/30; C12N 5/0018; C12N 5/0068
USPC .......... 422/63, 68.1, 52, 81, 100; 436/54, 180
See application file for complete search history.

(56) References Cited

U.S. PATENT DOCUMENTS 5,451,788 A * 9/1995 Pollack ..................... 250/361 C
(Continued)

OTHER PUBLICATIONS

"Basics of Turbulent Flow" (MIT Course): http://www.mit.edu/course/1/1.061/www/dream/SEVEN/SEVENTHEORY.PDF, pp. 1-10, no date.*

*Primary Examiner* — Yelena G Gakh
(74) *Attorney, Agent, or Firm* — PretiFlaherty, LLP

(57) ABSTRACT

Devices, systems, and methods for conducting chemiluminescent immunoassay testing and, more particularly, to initiating and monitoring a chemiluminescent reaction in a plurality of such assays, of different types, on a single immunoassay instrument, in a single procedure, using a plurality of labels and a triggering reagent combination are disclosed. Moreover, by including a base reagent injector assembly having an "e-channel" to provide a swirling turbulence to the base reagent immediately before it is introduced into the well of a cuvette containing a sample and an acid reagent. The added turbulence addresses the phenomenon referred to as "RLU shift," in which the luminescence output can increase or decrease between assays.

20 Claims, 6 Drawing Sheets

(52) U.S. Cl.
CPC ............... *B01L2400/0487* (2013.01); *G01N 2035/00514* (2013.01)

(56) References Cited

U.S. PATENT DOCUMENTS

| | | |
|---|---|---|
| 6,056,923 A | 5/2000 | Diamond et al. |
| 6,942,767 B1* | 9/2005 | Fazzina et al. ................. 204/252 |
| 7,198,754 B2* | 4/2007 | Kasahara et al. ........... 422/82.01 |
| 2004/0260242 A1* | 12/2004 | Hughes et al. ................. 604/140 |
| 2005/0074360 A1* | 4/2005 | DeWalch ........................ 422/63 |
| 2005/0180894 A1 | 8/2005 | Petroff et al. |
| 2006/0024201 A1* | 2/2006 | Bell ............................. 422/68.1 |
| 2008/0164199 A1* | 7/2008 | Seneviratne .................. 210/252 |

\* cited by examiner

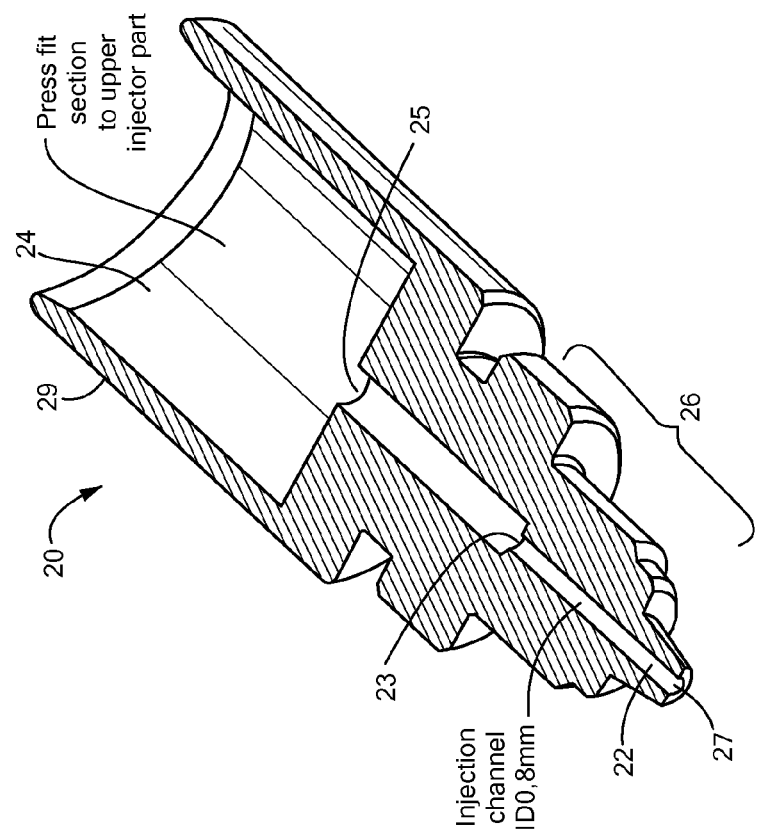
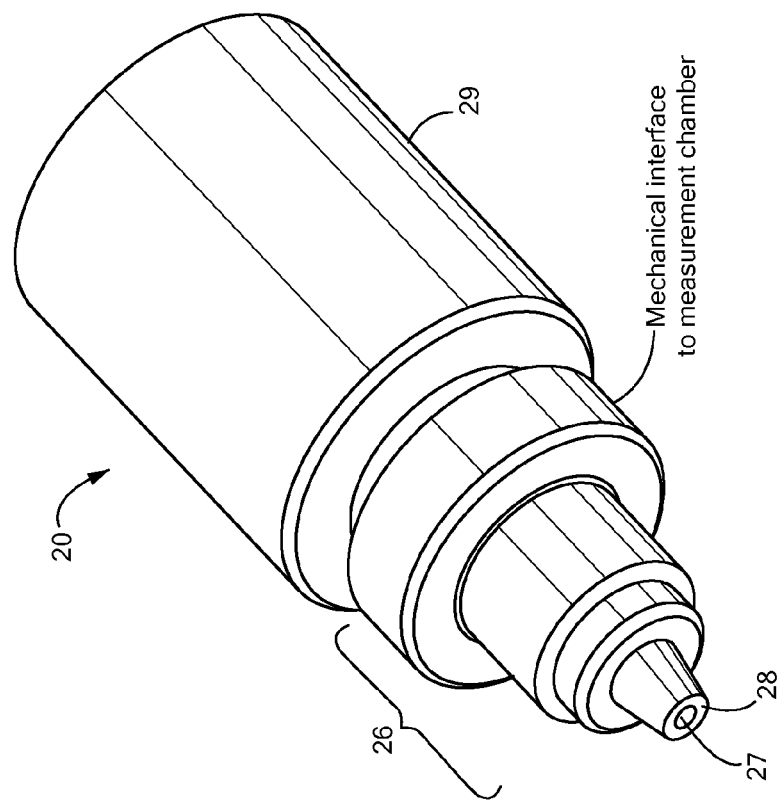
FIG. 2B
FIG. 2A

SYSTEM, DEVICE AND METHOD FOR REDUCING LUMINESCENCE OUTPUT SHIFTS

CROSS REFERENCE TO RELATED APPLICATIONS

This application claims the benefit of U.S. provisional patent application No. 60/737,650 filed on Nov. 17, 2005, which is incorporated herein in its entirety by reference.

STATEMENT REGARDING FEDERALLY SPONSORED RESEARCH OR DEVELOPMENT (Not Applicable)

BACKGROUND OF THE INVENTION

The present invention relates to means and methods for conducting chemiluminescent immunoassay testing and, more particularly, to initiating and monitoring a chemiluminescent reaction in a plurality of such assays, of different types, on a single immunoassay instrument, in a single procedure, using a plurality of analyte-specific, labeled reagents and a triggering reagent combination, wherein the phenomenon referred to as "RLU shift," in which the luminescence output can increase or decrease, is reduced or eliminated.

Assays are available to test a variety of body functions, including, for example, anemia, growth, thyroid, hypertension, tumor markers, neonatal conditions, the adrenal/pituitary system, bone and mineral metabolism, and the reproductive system. Immunoassay analyzers, such as chemiluminescent immunoassay analyzers, which automatically assay specimens, are one such device.

Chemiluminescence is a chemical reaction that emits energy in the form of light. The intensity of the luminescence when compared to a control intensity provides a measure of the concentration of the sample being tested. For example, during a chemiluminescent assay, a test sample and an analyte-specific, labeled reagent, such as an acridinium ester antigen or an acridinium ester antibody, are dispensed in a cuvette. Next, a solid phase reagent, such as paramagnetic particles having a binding substance coupled thereto, is added to the sample-containing cuvette. The sample-containing cuvette is then incubated.

During incubation, acridinium ester-labeled antibodies bind specifically to the antigen of interest in the sample. Alternatively, acridinium ester-labeled antigens compete with the antigen or interest already in the sample, to bind to the available antibody in the sample. Unbound labeled reagent is washed away.

Chemical reagents, often referred to as "trigger" reagents, are then added to the sample-containing cuvette to oxidize the analyte-specific, labeled reagent, or, more specifically, to initiate the chemiluminescent reaction. The trigger reagents, conventionally, include an acid reagent and a base reagent. First, an acid reagent, e.g., hydrogen peroxide, is dispensed into the sample-containing cuvette, to initiate oxidation. Then a base reagent is dispensed into the sample-containing cuvette, to alter the state of the environment from acidic to basic, which accelerates oxidation.

After the chemiluminescent reaction has been initiated, oxidation of the label to its excited state and its subsequent return to the ground state generates a flash, which typically lasts a few seconds. Conventionally, this flash is detected by a system-integrated luminometer. By examining the luminescence output resulting from mixing the test sample and trigger reagents, the automated analyzer can determine the concentration of the specific chemical constituent, for which the testing is being performed, in the patient's specimen.

More specifically, the luminescence output of the chemiluminescent reaction, i.e., the intensity of the flash, which is measured and expressed in relative light units (RLU), can be compared to a calibrated test standard, to determine the amount, for example, of bound, labeled antibody or antigen in the patient's blood.

Addition of a surfactant, such as a cationic detergent, to the base reagent is common. Advantageously, addition of a surfactant increases the intensity of light. However, when a surfactant is added, analyzers become susceptible to a phenomenon referred to as "RLU shift". During an "RLU shift", the luminescence output of the test sample can increase or decrease, which is to say "shift", by as much as fifteen or more percent. As a result, the measurements of specific chemical constituent concentration can be over- or under-estimated. This causes unacceptable total imprecision.

Therefore, it would be advantageous to be able to perform a plurality of such assays, of different types, on a single immunoassay instrument, in a single procedure, using a plurality of labels, and triggering reagents to initiate a chemiluminescent reaction for each of the labels sequentially.

SUMMARY OF THE INVENTION

The present invention provides for prevention of the RLU shift phenomenon by introducing various features into the fluidic subassembly that delivers base reagent (i.e., the base trigger reagent) to a reaction receptacle, such as a cuvette. More specifically, the present invention discloses a base reagent injector assembly that includes a channel in the shape of the letter "e" (hereinafter an "e-channel") and/or that is subject to sonic vibration.

BRIEF DESCRIPTION OF THE DRAWINGS

The invention will be better understood by reference to the following more detailed description and accompanying drawings where like reference numbers refer to like parts:

FIG. 2A shows a lower injector portion of a base injector assembly in accordance with the present invention;

FIG. 2B shows a cut-out of the lower injector portion of a base injector assembly in accordance with the present invention;

DETAILED DESCRIPTION OF THE INVENTION

Figure 1:
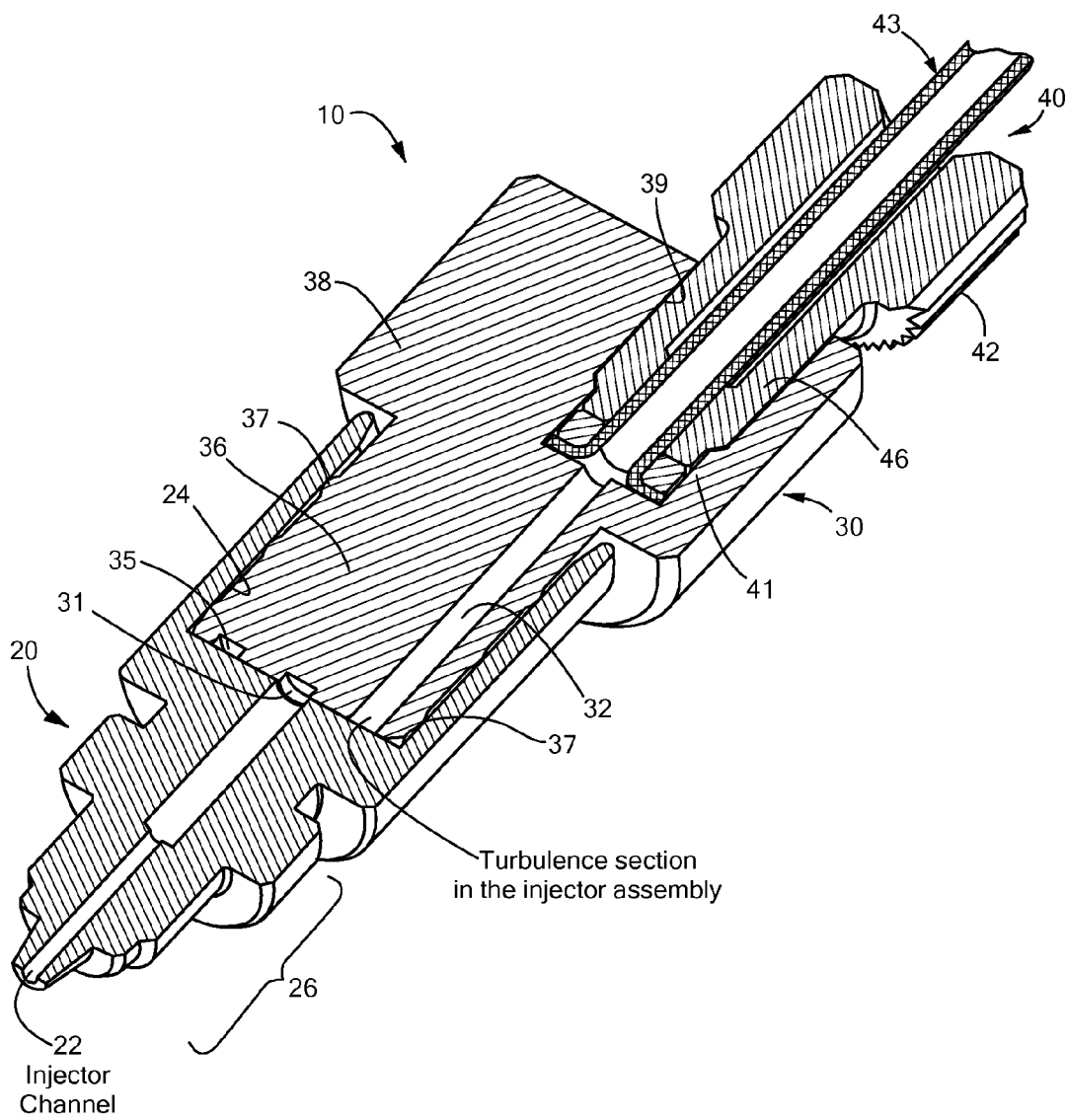
FIG. 1 shows a cut-out base injector assembly in accordance with the present invention.

As discussed above, automated chemiluminescent immunoassay analyzers are susceptible to a phenomenon known as "RLU shift", whereby the luminescence output from the flash, which is measured in RLUs, can increase or decrease by 15% or more from one assay run to the next. The mechanism(s) or factor(s) causing RLU shift, however, are not fully understood. Hence, the present inventor conducted empirical testing. The results and observations of the empirical testing are summarized below:

"RLU shift" is related to and caused by a base reagent pump transitioning from a "standby state" to a "ready state" or transitioning from a "ready state" to a "standby state", which transitions can be reproduced under controlled experimental conditions. In the "ready state", a stepper motor that drives the base reagent pump is energized. In the "standby state", the stepper motor is not energized. Thus, of all the factors potentially involved, the mechanism of the "RLU shift" involves the base reagent pump.

The magnitude of the luminescence signal is very sensitive to pump speed variations over a narrow range of pump speeds. For example, increasing the base reagent pump dispense speed from 950 to 1400 micro-liters per second (μl/sec) caused the luminescence to increase by about 20%. At a pump dispense speed above about 1400 μl/sec there was no increase in luminescence observed. Likewise, reducing the base reagent dispense speed from 950 to 700 μl/sec had no observable effect on luminescence.

Accordingly, in this narrow range of pump dispense speeds, which is to say, between about 950 and about 1400 μl/sec, the system is more sensitive to "RLU shift". In other words, within this narrow range of pump dispense speeds, the precision of repeated measurements is more susceptible to "RLU shift" than at pump dispense speeds above or below this narrow range. Thus, subtle variations in the dispense speed of the base reagent pump can cause substantial shifts in luminescence. For example, a 20% change in dispense speed may result in a 10% change in luminescence. The prior art does not suggest any correlation between pump dispense speed and luminescence and/or sensitivity when using, for example, a piston pump, driven by a stepper motor.

Evidence, therefore, suggests that the mechanism of an "RLU shift" involves the base reagent dispense step. This result, also, was unexpected, because, during a chemiluminescent immunoassay, the base reagent dispense step is tightly controlled and gross variations in the pattern or timing of the base reagent dispense, e.g., the speed and angle of dispensing the base reagent into the reaction liquid, were not observed. Nor does the prior art suggest that the base reagent dispense step is critical to achieve a reproducible luminescence signal.

Further experimentation revealed that the "RLU shift" can be mediated by adding a surfactant, e.g., a cationic detergent, to the base reagent solution, for the purpose of enhancing the luminescence signal. This result suggests that disruption of the micellar structure of the surfactant during the base reagent dispense step mediates the "RLU shift". The prior art is silent about micellar disruption affecting luminescence intensity.

Experimentation also demonstrated that an external source of vibration, when applied to base line, can mediate "RLU shifts". This result is consistent with a mechanism in which turbulence of the liquid flow in the base line—whether the turbulence is caused by the base reagent pump or by external vibration—causes disruption of the micelles, which enhances the chemi-luminescence.

The results of this testing suggest the following system model:

Between assay runs, when the system transitions to or from a standby state, the base reagent pump is switched from a smooth motion profile to a rough motion profile (or vice versa).

The change in pump state causes some change in the flow characteristics within the base line.

The altered flow of base reagent in the base line changes the structure of the micellar surfactant in a way that makes it more effective at enhancing the luminescence reaction.

Base Reagent Injector Assembly

Experimentation suggests that the "RLU shift" phenomenon, which occurs during a chemiluminescent reaction associated with an immunoassay system, can be prevented by "activating" the base reagent during the base reagent dispense step and/or, alternatively, by sonically vibrating the base fluid tubing during the base reagent dispense step. In short, prior to or at the time the base reagent is dispensed into the well of the sample-containing cuvette, the base reagent should be subject to turbulent flow.

The altered, i.e., turbulent, flow of the base reagent changes the structure of the micellar surfactant, which enhances the luminescent reaction and prevents "RLU shift".

A base reagent injector assembly 10 in accordance with the present invention is shown in FIG. 1. The base reagent injector assembly 10 includes a lower injector portion 20 and an upper injector portion 30. The lower injector portion 20 is structured and arranged to be mechanically- and fluidly-coupled to a measurement unit (not shown). The upper injector portion 30 is structured and arranged to be mechanically- and fluidly-coupled to injector tubing 40.

Referring to FIG. 2A and FIG. 2B, the lower injector portion 20 will be described. The lower injector portion 20 includes a hollow, cylindrical body 29, a measurement unit interface 26, and a nozzle 28. The hollow, cylindrical body 29 includes a chamber cavity 24 that is structured and arranged to accommodate the protrusion portion 36 of the upper injector portion 30 (described below). More specifically, the chamber cavity 24 of the hollow, cylindrical body 29 is structured and arranged to have an inner, peripheral circumference that provides a tight, interference (press) fit with a plurality of seal rings 37 disposed on the outer periphery of the protrusion portion 36 of the upper injector portion 30.

A channel opening 25 is provided at or near the center of the chamber cavity 24. The channel opening 25 is fluidly-coupled to the outlet 27 of the nozzle 28 via an injection channel 22. An exemplary length of the injector channel 22 for a prototype used in testing was about 0.33 inches (8 mm). The inner diameter (ID) of the injector channel 22 includes a step-down transition 23 from about 0.043 inches (about 1.1 mm) to about 0.033 inches (about 0.8 mm). The diameter step-down transition 23 introduces more turbulence to the base reagent fluid passing through the injector channel 22.

Figure 3A:
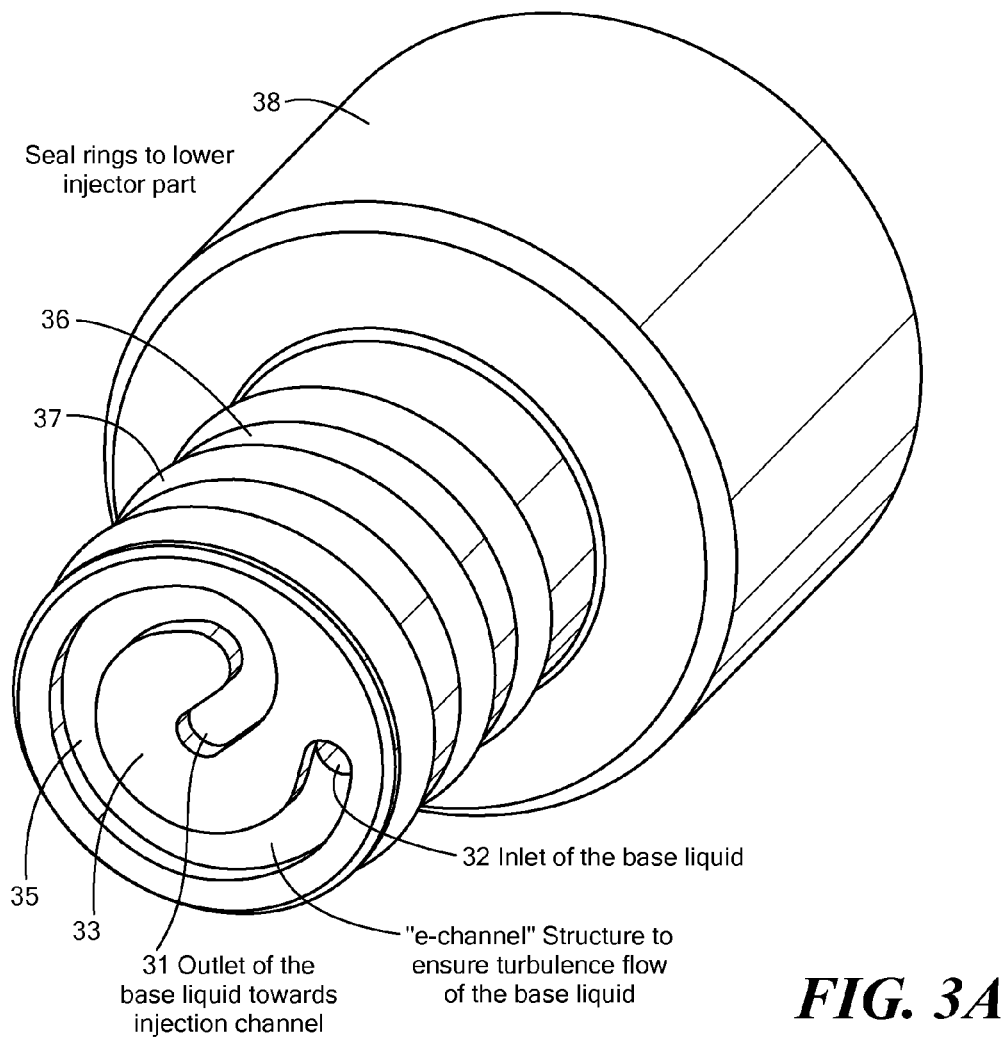
FIG. 3A shows an upper injector portion of a base injector assembly in accordance with the present invention.
Figure 3B:
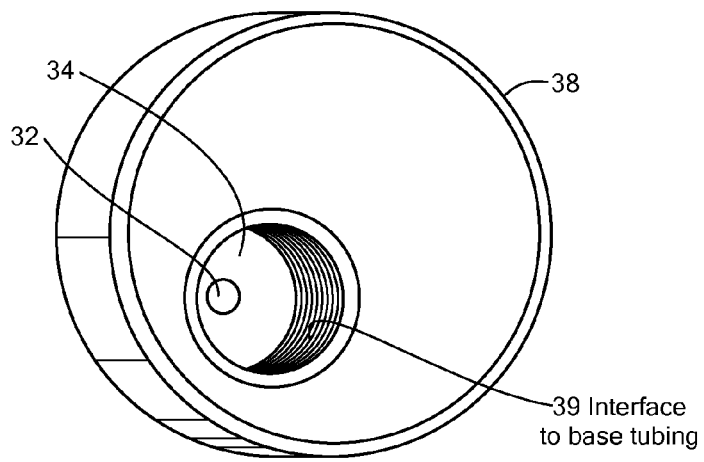
FIG. 3B shows a cut-out of the upper injector portion of a base injector assembly in accordance with the present invention.
Figure 6:
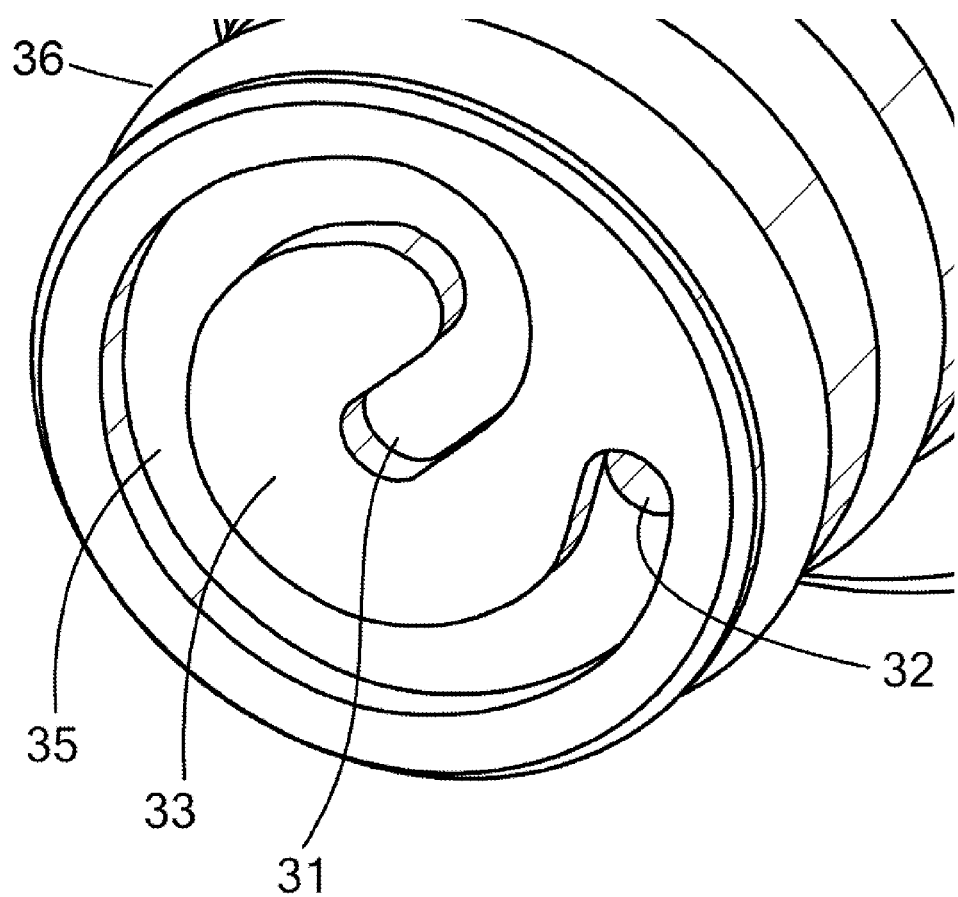
FIG. 6 is a black and white line drawing of the enlarged view of FIG. 3A.

Referring to FIG. 3A, FIG. 3B, and FIG. 6, an upper injector portion 30 will be described. The upper injector portion 30 includes a cylindrical protrusion portion 36 and a cylindrical body portion 38. The cylindrical protrusion portion 36 is structured and arranged to mate with, i.e., to provide a tight interference (press) fit with, the lower injector portion 20. The cylindrical body portion 38 is structured and arranged to mate with injector tubing 40.

The cylindrical protrusion portion 36 is concentric with and fixedly attached to a proximal end of the body portion 38. The distal end of the body portion 38 includes an injector tubing interface 34 for releasably attaching injector tubing 40 to the body portion 38 of the upper injector portion 30. More specifically, spiral threadings 39 are provided on the peripheral surface of the injector tubing interface 34 to accommodate associated threadings 46 disposed on a first end 41 of the injector tubing 40 (shown in FIG. 4). The injector tubing interface 34 is, preferably, not coaxial with the cylindrical body portion 38.

An opening 32 is provided at or near the center of the injector tubing interface 34. Because the injector tubing interface 34 is not coaxial with the cylindrical body portion 38, the opening 32 is also off-set from the center of the cylindrical body portion 38. The opening 32 is fluidly-coupled to an outlet 31 disposed on the face 33 of the protrusion portion 36 via an e-shaped channel, or "e-channel" 35.

The "e-channel" 35 traverses through the protrusion portion 36, from the opening 32 to the outlet 31. An exemplary inner diameter (ID) of the opening 32 and the "e-channel" 35 is about 0.06 inches (about 1.5 mm). The outlet 31 is structured and arranged to be in registration with the channel opening 25 in the lower injector portion 20 when the upper and lower injector portions 30 and 20 are press-fitted together.

The "e-channel" 35 is adapted to provide swirling turbulence to the base reagent fluid passing through the upper injector portion 30. Although this disclosure refers to the channel providing swirling turbulence as an "e-channel", the channel can take on any shape so long as it provides swirling turbulence. For example, in lieu of an e-shaped channel, the channel can be structured and arranged to include at least two rather abrupt, 90 degree changes in direction. In the e-channel embodiment depicted in FIG. 3A and FIG. 6, fluid flow turns 90 degrees as it passes out of the opening 32 into the e-channel 35, and again as it passes from the e-channel 35 through the outlet 31. By undergoing abrupt, orthogonal changes in flow direction, the base reagent fluid is "activated", i.e., is in a turbulent flow state, prior to entering the injection channel 22 of the lower injector portion 20.

The cylindrical protrusion portion 36 includes a plurality of seal rings 37 for providing a tight, interference (press) fit in the cavity 24 of the lower injector portion 20. Although FIG. 1 and FIG. 3A show three seal rings 37 on the protrusion portion 36, more or fewer seal rings 37 can be included without violating the scope and spirit of this disclosure.

Chemiluminescent Immunoassay System

Figure 5:
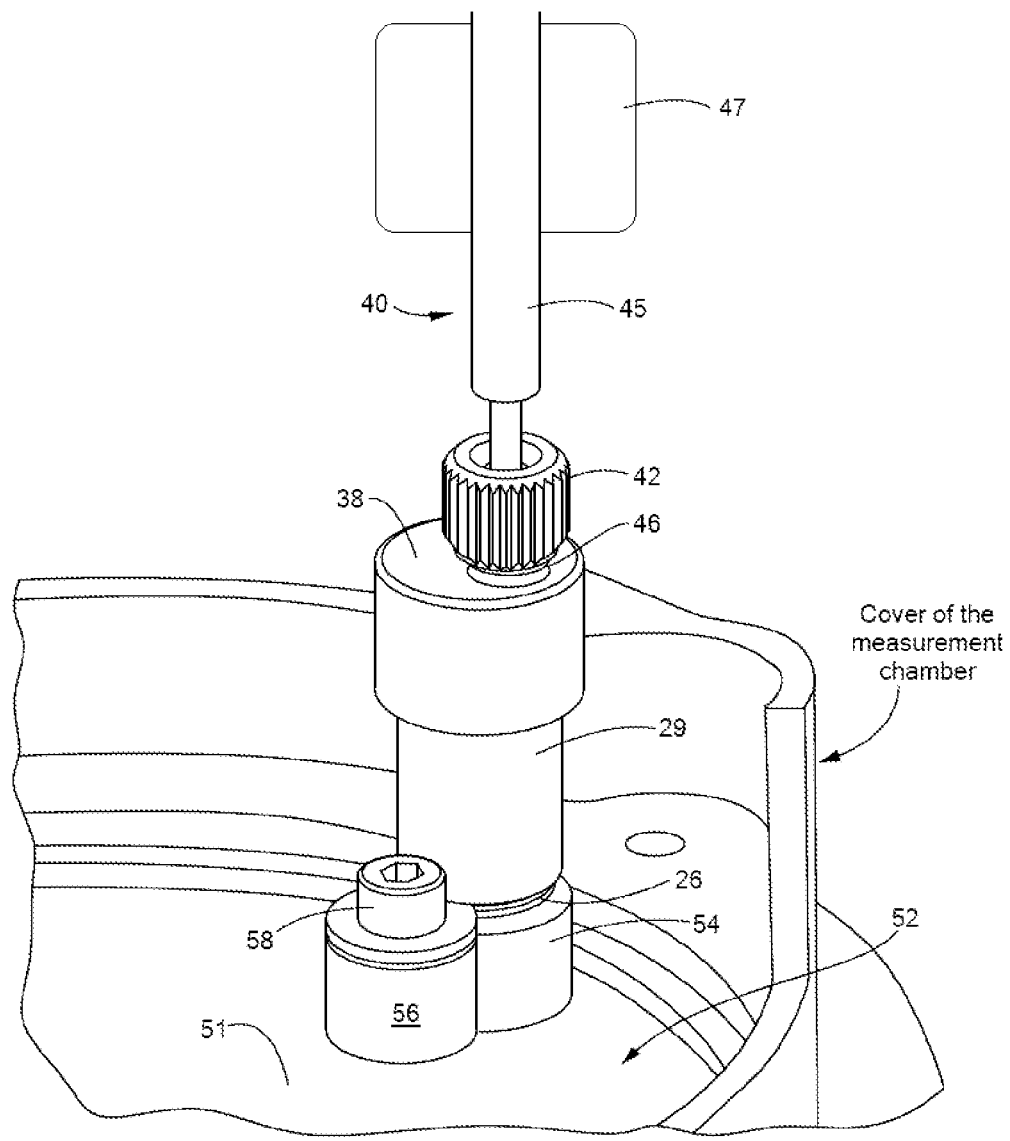
FIG. 5 shows a base injector assembly and measurement chamber in accordance with the present invention.

Referring to FIG. 5, a chemiluminescent immunoassay system 50 using the base reagent injector assembly 20 will be described. The system 50 includes injector tubing 40 for providing base reagent, the base reagent injector assembly 10, and a measurement unit 52. A first end 41 of the injector tubing 40 is mechanically- and fluidly-coupled to the upper injector portion 38 via the injector tubing interface 34. More specifically, the injector tubing 40 is structured and arranged so that the outlet (not shown) of the injector tubing 40 is in registration with the opening 32 in the injector tubing interface 34.

The measurement unit interface 26 of the lower injector portion 20 is mechanically- and fluidly-coupled to the measurement unit 52 via a mechanical interface 54 that is disposed on the cover 51 of the measurement unit 52. Proximate to the mechanical interface 52 is a fitting screw interface 56 that is structured and arranged to mate with an eccentric, fitting screw or bolt 58 for further tightening the fit between the measurement unit interface 26 and the mechanical interface 54.

Figure 4:
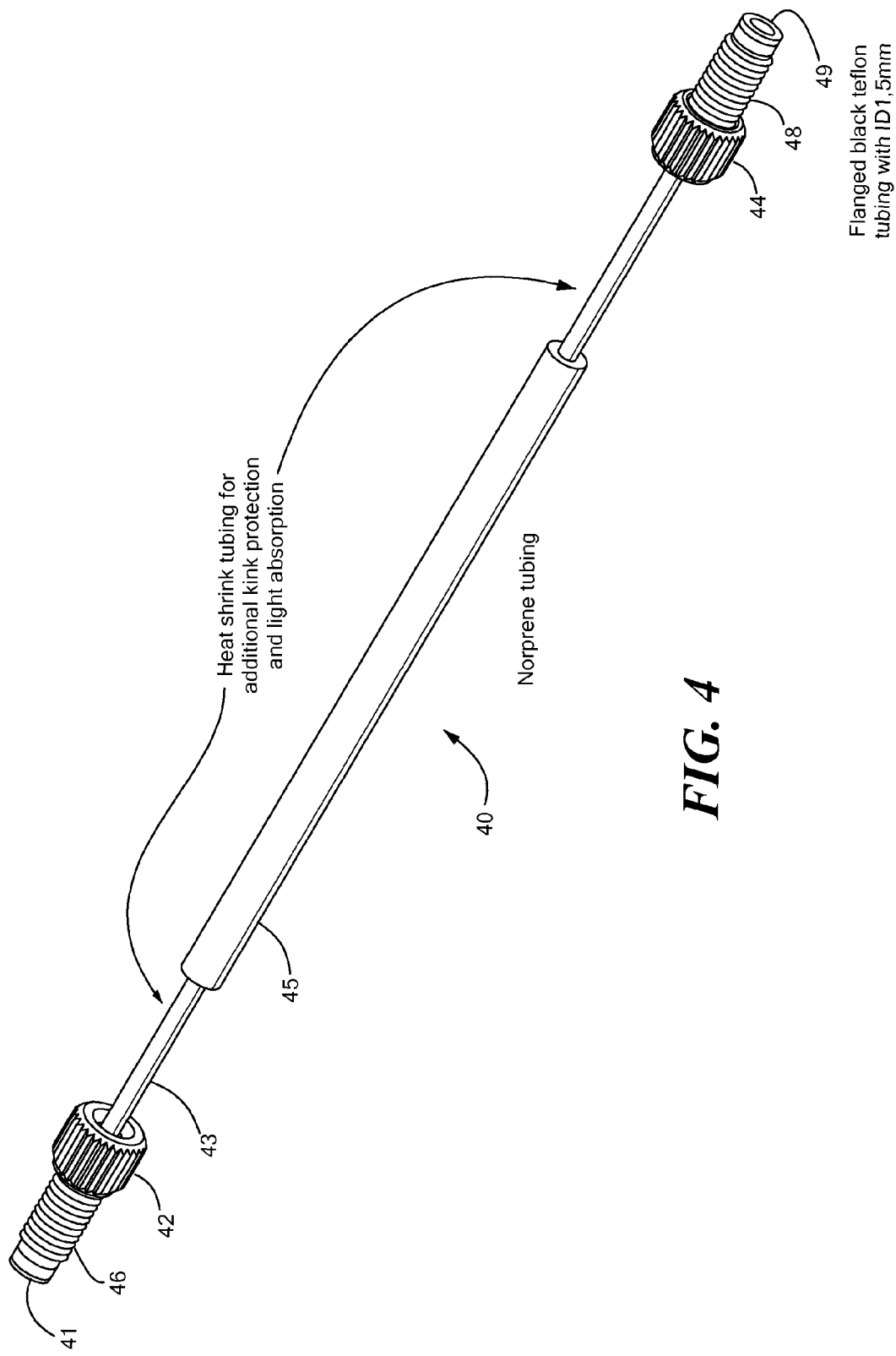
FIG. 4 shows an injector tubing in accordance with the present invention.

Referring to FIG. 4, injector tubing 40 for use with the chemiluminescent immunoassay system 50 will now be described. The injector tubing 40 includes a first end 41 and a second end 49. The injector tubing 40 can be made of black Teflon® tubing 43 (manufactured by DuPont Corp. of Wilmington, Del.) having a Norprene® cover 45 (manufactured by Saint-Gobain Performance Plastics Corp. of Aurora, Ohio). The black tubing 43 protects the base reagent fluid from light and the cover 45 prevents kinked tubing. Optionally, black heat shrink material (not shown) can be included on the outside of the tubing 43 proximate to the fitting screws 46 and 48.

The ends 41 and 49 of the tubing 43 are flanged. The tubing 43 has an inner diameter of about 0.06 in. (about 1.5 mm). For mechanically-attaching the injector tubing 40 to the upper injector portion 30, fitting screws 46 and 48 and press rings 42 and 44, which are well known to those skilled in the art, are provided.

Optionally, the system 50 can include vibration means 47 adapted to apply sonic vibrations to the injector tubing 40, to induce turbulence in the base reagent fluid. For example, the injector tubing 40 can be operationally-coupled to a small loudspeaker 47 (about 200 mW). More specifically, the injector tubing 40 can be adhesively attached to the center of the diaphragm of the loudspeaker 47. A pulse generator provides sonic vibrations to the injector tubing 40 via the loudspeaker 47. The pulse generator is adapted to generate a tone at a frequency between about 280 Hz and about 1000 Hz having an amplitude of about 5V (peak-to-peak).

Method of Conducting Chemiluminescent Assays

Having described a chemiluminescent immunoassay system 50 and a base reagent injector assembly 20 therefor, a method of conducting chemiluminescent assays and, more particularly, for actively dispensing a base reagent into a reaction liquid so as to prevent "RLU shift" will now be described. Protocols for conducting chemiluminescent assays are well known to the art and will not be described in detail herein.

According to the present invention, a cuvette, having a well that contains an acid trigger reagent and a test sample that has been labeled using, for example, luminol or acridinium, is loaded into a measurement unit. A background measurement of the luminescence of the test sample is, typically, taken to establish a base line. After the background measurement, while the test sample is still in the measurement unit, a base reagent is added to the well of the cuvette, which triggers a chemiluminescent reaction with the label. As provided above, the base reagent is added to the cuvette in a turbulent flow condition so that the structure of the micellar surfactant in the base reagent is changed. Injecting the triggering (base) reagent under turbulent flow conditions tangentially along or against the walls of the cuvette well washes down any of the sample or of the acid reagent thereon. As a result, cross-contamination caused by the triggering (base) reagent exiting the nozzle of the base reagent injector assembly is substantially eliminated.

The base reagent liquid can be placed in a turbulent flow condition by one or more of the "e-channel" in the upper injector portion, the step-down diameter in the lower injector portion, and/or sonically vibrating the injector assembly.

The luminescence can then be measured, e.g., using a photomultiplier tube (PMT). Typically, the reaction liquid in the well of the cuvette is aspirated and discarded and the emptied cuvette is removed from the measurement unit.

The invention has been described in detail including the preferred embodiments thereof. However, those skilled in the art, upon considering the present disclosure, may make modifications and improvements within the spirit and scope of the invention.

What we claim is:

1. A base reagent injector assembly for reducing Relative Light Unit (RLU) shift in chemiluminescent reactions, the injector assembly for dispensing a base reagent into a reaction receptacle for a chemiluminescent immunoassay test, the injector assembly comprising:

a lower injector portion having a proximal end, the proximal end configured to mechanically- and fluidly-couple to a RLU measurement unit, the lower injector portion further comprising a distal end, an injection channel, and a nozzle, the distal end having a chamber cavity; and an upper injector portion having a cylindrical proximal end configured to releasably- and mechanically-couple to the lower injector portion when inserted into the chamber cavity, and the upper injector portion comprising a feed channel, the feed channel having an inlet and an outlet, therethrough, wherein the outlet of the feed channel is configured to be in registration with the injection channel of the lower injector portion when the upper injector portion is releasably- and mechanically-coupled to the lower injector portion, the feed channel is configured to create swirling turbulent flow in the base reagent before said base reagent is introduced into the injection channel, and the creation of the swirling turbulent flow is insensitive to pump speed variations within a range of pump dispense speeds.

2. The injector assembly as recited in claim 1, the injection channel of the lower injector portion has a first inner diameter in registration with the outlet of the feed channel and a second inner diameter at an opening in the nozzle, wherein the first inner diameter is larger than the second inner diameter.

3. The injector assembly as recited in claim 2, wherein the first inner diameter is about 0.043 inches (about 1.1 mm) and the second inner diameter is about 0.033 inches (about 0.8 mm).

4. The injector assembly as recited in claim 1, wherein the cylindrical proximal end of the upper injector portion includes a plurality of seal rings configured to provide a tight, interference fit with the chamber cavity of the lower injector portion when the upper injector portion is releasably- and mechanically-coupled to the lower injector portion.

5. The injector assembly as recited in claim 1, wherein the feed channel has a spiral shape, the inlet located radially outward from a center of the spiral shape and the outlet located at the center of the spiral shape.

6. The injector assembly as recited in claim 1, wherein the feed channel includes at least two 90 degree changes in direction.

7. The injector assembly as recited in claim 1, wherein the injector assembly further comprises: injector tubing in registration with the inlet of the feed channel, and a vibrator configured to operationally-couple to the injector tubing and to provide turbulence-inducing vibrations to the injector tubing.

8. The injector assembly as recited in claim 7, wherein the vibrator comprises:

a loudspeaker configured to couple to the injector tubing; and a pulse generator configured to generate a pulse for selectively driving the loudspeaker.

9. The injector assembly as recited in claim 8, wherein the pulse generator is adapted to generate pulses at a frequency between about 280 Hertz and 1000 Hertz.

10. The injector assembly as recited in claim 1, wherein the injection channel of the lower injector portion and the inlet of the feed channel of the upper injector portion have respective axes that are not coaxial when the upper injector portion is releasably- and mechanically-coupled to the lower injector portion.

11. A chemiluminescent immunoassay testing system comprising:

a measurement unit configured to measure chemiluminescence of a sample after introduction of an acid reagent and a base reagent into a cuvette containing the sample; and an injector assembly, adapted to reduce chemiluminescent Relative Light Unit (RLU) shift, comprising:

a lower injector portion having a proximal end, the proximal end configured to mechanically- and fluidly-couple to the measurement unit, the lower injector portion further comprising a distal end, an injection channel, and a nozzle, the distal end having a chamber cavity; and an upper injector portion having a cylindrical proximal end configured to releasably- and mechanically-couple to the lower injector portion when inserted into the chamber cavity, and the upper injector portion comprising a feed channel, the feed channel having an inlet and an outlet, therethrough, wherein the outlet of the feed channel is configured to be in registration with the injection channel of the lower injector portion when the upper injector portion is releasably- and mechanically-coupled to the lower injector portion, the feed channel is configured to create swirling turbulent flow in the base reagent before said base reagent is introduced into the injection channel, and the creation of the swirling turbulent flow is insensitive to pump speed variations within a range of pump dispense speeds.

12. The chemiluminescent immunoassay testing system as recited in claim 11, wherein the measurement chamber includes a photomultiplier tube configured to measure chemiluminescence.

13. The chemiluminescent immunoassay testing system as recited in claim 11, wherein the injector assembly further comprises: injector tubing in registration with the inlet of the feed channel, and a vibrator configured to operationally-couple to the injector assembly and adapted to provide turbulence-inducing vibrations to the injector assembly.

14. The chemiluminescent immunoassay testing system as recited in claim 13, wherein the vibrator includes:

a loudspeaker configured to couple to the injector tubing; and a pulse generator configured to generate a pulse for selectively driving the loudspeaker.

15. The chemiluminescent immunoassay testing system as recited in claim 14, wherein the pulse generator is adapted to generate pulses at a frequency between 280 Hertz and 1000 Hertz.

16. The chemiluminescent immunoassay testing system as recited in claim 11, wherein the injection channel of the lower injector portion and the inlet of the feed channel of the upper injector portion have respective axes that are not coaxial when the upper injector portion is releasably- and mechanically-coupled to the lower injector portion.

17. An upper injector portion of a injector assembly, the upper injector portion comprising:

a cylindrical proximal end configured to couple to a lower injector portion;

a spiral-shaped feed channel comprising an inlet and an outlet, the feed channel configured to create a swirling turbulent flow in a fluid passing from the inlet to the outlet, wherein the swirling turbulent flow is created when the fluid is passing from the inlet to the outlet within a range of pump dispense speeds and is insensitive to pump speed variations; and a distal tubing interface configured to attach to an injector tubing, wherein the outlet of the feed channel is configured to be in registration with an injection channel of the lower injector portion when the upper injector portion is coupled to the lower injector portion.

18. The upper injector portion as recited in claim 17, wherein the feed channel includes at least two abrupt 90 degree changes in direction.

19. An injector assembly for dispensing a fluid into a reaction receptacle for a chemiluminescent immunoassay test, the injector assembly comprising:
- a lower injector portion having a proximal end, the proximal end configured to couple to a measurement unit, the lower injector portion further comprising a chamber cavity; and
- an upper injector portion having a cylindrical proximal end inserted into the chamber cavity and coupled to the lower injector portion, and the upper injector portion comprising a spiral-shaped feed channel, the feed channel having an inlet and an outlet,
- wherein the outlet of the feed channel is in registration with the injection channel of the lower injector portion, and
- the injector assembly is configured to change a structure of a micellar surfactant in the fluid before the fluid is introduced into the injection channel such that the change is insensitive to pump speed variations within a range of pump dispense speeds.

20. The upper injector portion as recited in claim 19, wherein the injector assembly further comprises: injector tubing coupled to the inlet of the feed channel and configured to supply fluid to the inlet; and a vibrator coupled to the injector tubing and configured to provide vibrations to the fluid in the injector tubing.

* * * * *